United States Patent [19]

Hitti

[11] Patent Number: 5,348,007
[45] Date of Patent: Sep. 20, 1994

[54] BIOMEDICAL ELECTRODE
[75] Inventor: Raja Hitti, Utica, N.Y.
[73] Assignee: Conmed Corporation, Utica, N.Y.
[21] Appl. No.: 36,336
[22] Filed: Mar. 24, 1993
[51] Int. Cl.5 ............................................ A61B 5/0402
[52] U.S. Cl. ................................................... 128/640
[58] Field of Search ............................. 128/639–641, 128/644; 607/149, 152, 153

[56] References Cited

U.S. PATENT DOCUMENTS

| | | | |
|---|---|---|---|
| 3,662,757 | 5/1972 | Blackett | 607/152 |
| 4,331,153 | 5/1982 | Healy . | |
| 4,657,023 | 4/1987 | Kuhn . | |
| 4,674,511 | 6/1987 | Cartmell | 128/640 |
| 4,674,512 | 6/1987 | Rolf . | |
| 4,763,660 | 8/1988 | Kroll et al. | 128/640 |

FOREIGN PATENT DOCUMENTS

| | | | |
|---|---|---|---|
| 1441622 | 7/1976 | United Kingdom | 128/639 |
| 1587817 | 4/1981 | United Kingdom | 128/639 |

Primary Examiner—Lee S. Cohen
Attorney, Agent, or Firm—Larson & Taylor

[57] ABSTRACT

An electrode for establishing electrical connection between a leadwire and a surface includes a contact portion and a conductive bridge portion. The contact portion includes a conductive layer, an insulator layer on one side thereof, and an anchor or adhesive layer on the other side thereof for anchoring the contact portion to the surface. The bridge portion extends from the contact portion and is electrically connected with the conductive layer. The bridge portion includes a receptor to which the leadwire is attachable and a series of perforations which form a breakaway or yieldable connection mechanism for allowing the bridge portion to be partially pulled apart when applied to the surface. The series of perforations thus allow the receptor to move yieldably with six degrees of freedom of movement relative to the contact portion while still maintaining electrical connection with the conductive layer. Thus, when a pulling force is exerted between the leadwire and the contact portion, the exerted force is relieved without pulling the contact portion from the surface. Preferably, the bridge portion and receptor are an extension of the conductive layer and insulator layer beyond an end of the anchor layer. The receptor is also preferably forms a tab which is moved from a plane of the extension. The series of perforations ends in a circular aperture and forms a coil, though the series could also be at least two straight lines.

20 Claims, 2 Drawing Sheets

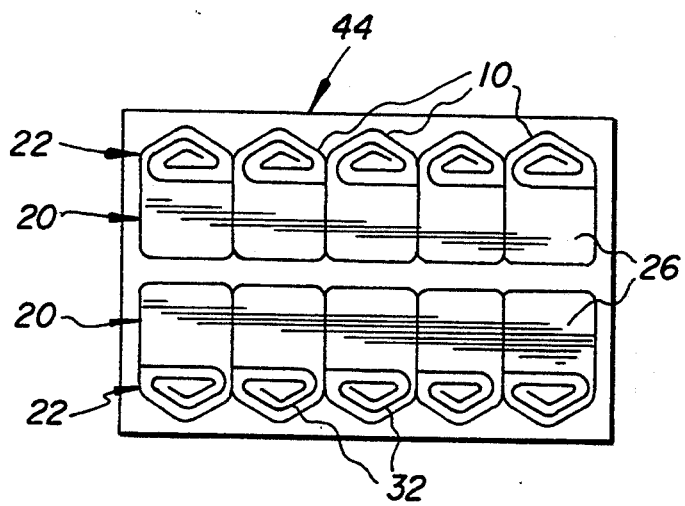
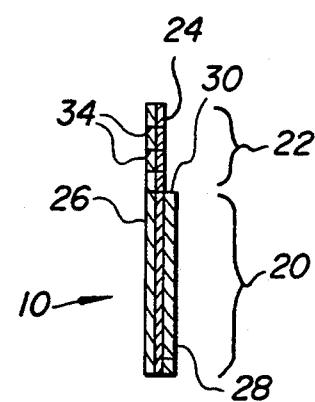
Fig. 5  Fig. 2
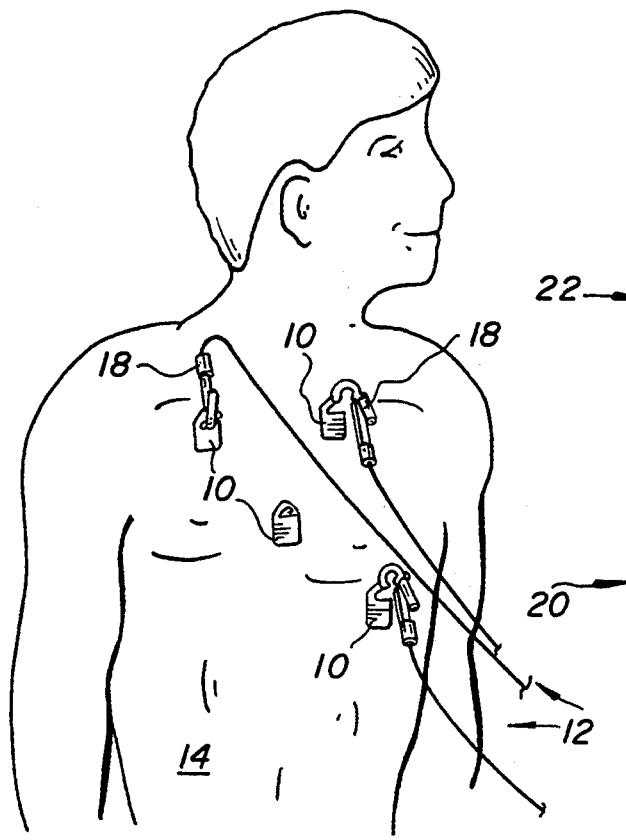
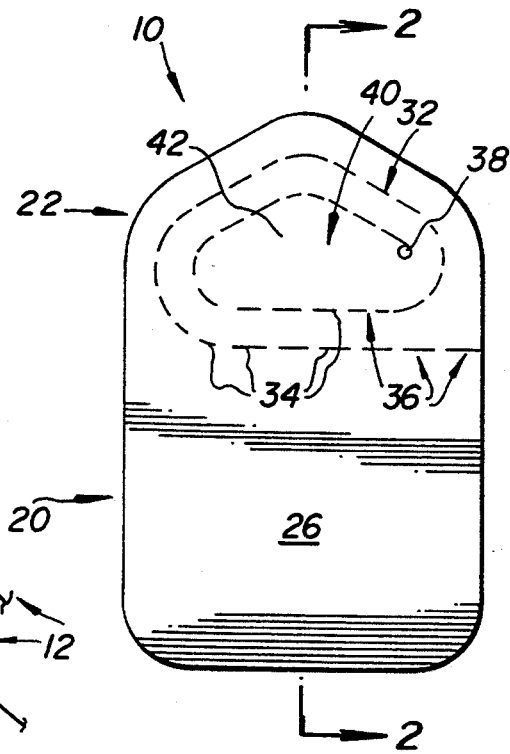
Fig. 6  Fig. 1

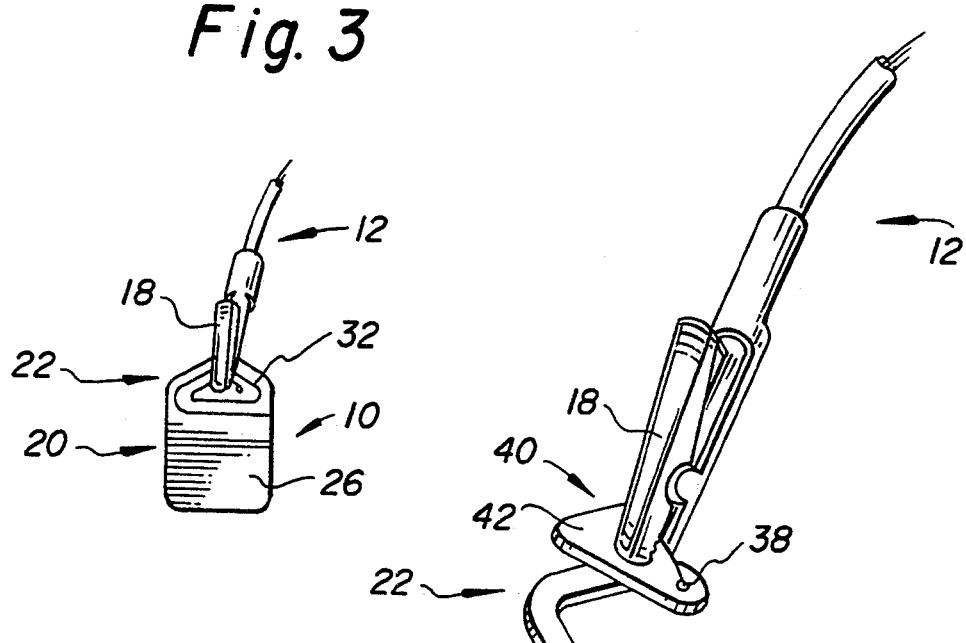
Fig. 3
Fig. 4
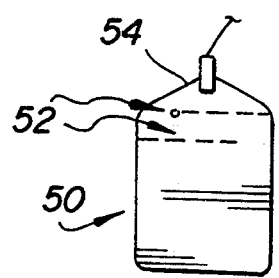
Fig. 7
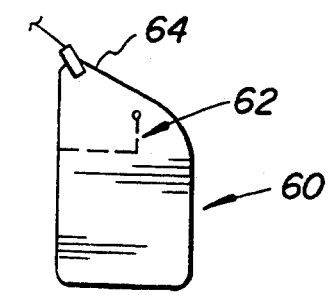
Fig. 8

5,348,007

BIOMEDICAL ELECTRODE

FIELD OF THE INVENTION

The present invention relates generally to biomedical electrodes which electrically connect a leadwire to the skin of a patient, and more particularly to a biomedical electrode which will not easily be pulled from the skin when a force is exerted between the leadwire and the patient.

BACKGROUND OF THE INVENTION

Biomedical electrodes are typically used in electrocardiography and like diagnostic procedures as well as for long term monitoring where a patient must be electrically connected to a test or monitoring device. Such electrodes often consist of three distinct layers: a conductive surface layer of about one square inch, an insulator on one side of the conductive surface layer with graphics imprinted thereon, and a medical gel provided on the other side of the conductive surface layer. The medical gel is used to anchor the electrode to the skin of the patient. The conductive surface layer can be a metallic layer or even conductive ink.

In use, the leadwires of an ECG (or like device) typically include clips or the like at the end thereof which are attached to dedicated connection portions or projections of the electrodes. Such connection portions can be shaped as a mitten (thumb imprint - semi circular) or a fish tail and may be located where the medical gel is absent. Due to the relatively large size (and weight) of the leadwire compared to the electrode, coupled with the inherent tendency of the leadwire to coil, a pulling force is often exerted on the electrode which may peal the electrode from the skin as the medical gel is only a somewhat weak adhesive. There also frequently arises pulling forces as a result of patient movement, both as a result of desired movements and unintended movements. Besides a full pealing off, the force may also only disturb or partially peal the electrode from the skin, resulting in distorted signals (as by noise or artifact) and unusable results. In any event, time and effort are wasted. Further, once an electrode is pealed off, or partially pealed off, it may not be capable of being reanchored properly so that a new electrode must then be used.

SUMMARY OF THE INVENTION

In accordance with the present invention, an electrode for establishing electrical connection between a leadwire and a surface includes a contact portion and a conductive bridge portion. The contact portion includes a conductive layer, an insulator layer on one side of the conductive layer, and an anchor means or adhesive layer on the other side of the conductive layer for anchoring the contact portion to the surface. The conductive bridge portion extends from the contact portion and is electrically connected with the conductive layer. The bridge portion includes a receptor to which the leadwire is attachable and a breakaway means for allowing the bridge portion to be partially pulled apart when applied to the patient. The broken away bridge portion thus allows the receptor to move relative to the contact portion while still maintaining electrical connection with the conductive layer. Thus, when a pulling force is exerted on the bridge portion the exerted force is relieved by movement of the bridge portion without pulling (or partially pulling) the contact portion from the surface.

In a preferred embodiment of the invention, the bridge portion is an extension of the conductive layer and of the insulator layer beyond an end of the anchor means. The receptor is also a portion of the extension of the conductive layer and insulator layer which forms a tab which is raised from a plane of the extension of the conductive layer and the insulator layer.

In the preferred embodiment, the breakaway means is a series of perforations in the bridge portion which ends in a circular aperture. The series of perforations also preferably forms a coil, though the series could also be at least two straight lines or variations thereof.

Also in accordance with the present invention, an electrode for establishing electrical connection between a leadwire and a surface includes a flexible contact portion as discussed above and a conductive bridge portion extending from the contact portion and electrically connected with the conductive layer. This bridge portion includes a receptor to which the leadwire is attachable and a yielding connection means. The yielding connection means electrically and yieldably connects the receptor to the contact portion while allowing the receptor to move with six degrees of freedom relative to the contact portion. When a force is applied between the leadwire and the contact portion, this movement of the receptor helps to relieve the exerted force without pulling the contact portion from the surface.

Preferably, the bridge portion includes at least one tear means for allowing the extension to tear at predetermined locations to form the yielding connection means. Conveniently, the tear means is a series of perforations in the extension, which may form a coil ending in a circular aperture.

It is a object of the present invention to provide an electrode which is easily and quickly attached to the skin of the patient.

It is also an object of the present invention to provide an electrode which remains attached to the skin of the patient despite the inevitable pulling forces exerted by the leadwire and movements of the patient.

It is still another object of the present invention to provide an electrode with a bridge portion which can be torn apart to provide a relief mechanism for pulling forces exerted on the electrode.

Other features, objects and advantages of the present invention are stated in or apparent from detailed descriptions of presently preferred embodiments of the invention found hereinbelow.

BRIEF DESCRIPTION OF THE DRAWINGS

FIG. 1 is a top plan view of an electrode of the present invention.

FIG. 2 is a cross-section view of the electrode depicted in FIG. 1 taken along the line 2—2.

FIG. 3 is a schematic plan view of the electrode depicted in FIG. 1 with a leadwire attached thereto.

FIG. 4 is a perspective view of the electrode depicted in FIG. 3 which has been subjected to a pulling force.

FIG. 5 is a schematic plan view of a holder of a plurality of the electrodes depicted in FIG. 1.

FIG. 6 is a schematic view of a patient with a plurality of the electrodes depicted in FIG. 1 attached thereto.

FIG. 7 is a schematic plan view of an alternative embodiment of an electrode of the present invention.

FIG. 8 is a schematic plan view of another alternative embodiment of an electrode of the present invention.

DETAILED DESCRIPTION OF THE PREFERRED EMBODIMENTS

With reference now to the drawings in which like numerals represent like elements throughout the views, a flexible biomedical electrode 10 according to a first preferred embodiment of the present invention is depicted in FIGS. 1–4. Electrode 10 is designed for providing electrical connection between a leadwire 12 and the suitable surface, such as the skin surface 14 of a patient. Leadwire 12 in the depicted embodiments includes a suitable a clip 18 which is used to attach leadwire 12 electrically to electrode 10.

Electrode 10 includes two portions, a contact portion 20 and a conductive bridge portion 22. Contact portion 20 is formed of a plurality of flexible or compliant layers. One layer is a conductive layer 24. Conductive layer 24 is typically formed of either a metallic (or metallic-like, or otherwise conductive) foil (such as aluminum or lab-grade tin, 0.001" thick) or a conductive ink (such as silver chloride or other conductive ink combinations). Conductive layer 24 is suitably attached on one side to (or printed on) a carrier or insulator layer 26. Insulator layer 26 is typically printed on the other side with the logo of the company and is typically made from a clear or white polyester which is 0.002" or more thick. Instead of polyester, either a spunbound polyester ("cloth" feel), polyethylene (or other) foam, paper or paper derivatives, TYVEK material, or other suitable carrier materials can be used. If a conductive ink is used, the ink can be applied to insulator layer 24 over the complete surface, or in a pattern if desired. The final layer of contact portion 20 is an anchor means or layer 28. Anchor layer 28 is used to anchor electrode 10 to the surface of interest, and in the case of a skin surface 14 is typically a conductive medical gel well known in the art.

It will be appreciated that anchor layer 28 terminates in an end 30, so that an extension of both conductive layer 24 and insulator layer 26 beyond end 30 forms bridge portion 22 as best shown in FIG. 2. Provided in bridge portion 22 is a series 32 of perforations or slits 34 separated by small connections 36. Series 32 begins at one side of electrode 10 and forms a coil which is triangular/circular shaped. Series 32 ends at a circular aperture 38 having a small diameter such as 1/32".

It will also be appreciated that the center of bridge portion 22 forms a receptor 40 to which clip 18 is attached. In particular, by pulling on receptor 40 and breaking the small connections 36 between perforations 34 adjacent thereto, a small tab 42 is lifted from the plane of bridge portion 22 for easy attachment of clip 18 as shown in FIG. 3. Tab 42 can be provided in a variety of shapes besides the triangular one shown, such as rectangular, elliptical or others (with or without the coil shape being similarly configured). The presence of circular aperture 32 also serves to prevent further and unwanted tearing of bridge portion 22 when tab 42 is lifted.

In use, series 32 of perforations 34 forms a breakaway means for bridge portion 22 which is used to pull bridge portion 24 apart either immediately before or after contact portion 20 is applied to skin surface 14. Thus, a yieldable bridge portion or connection means is provided which acts as a force or strain relief mechanism due to the fact that the coil or spiral is itself somewhat resilient. This resiliency is due to the nature of the material of insulator layer 26, and the material of insulator 26 is also chosen to be of sufficient strength to withstand further tearing once connections 36 are broken. In the use position, clip 18 is also easily attached to tab 42 once small connections 36 between perforations 34 have been broken (i.e., bridge portion 22 is at least partially uncoiled).

Consequently, should any force or strain be exerted between leadwire 12 and skin surface 14 which would be sufficient or tend to pull or twist contact portion 20 of electrode 10 from skin surface 14, the force instead causes, as depicted in FIG. 4, the expansion as by uncoiling or pulling of bridge portion 22. As a result, the coil which is one to two inches in length is able to absorb or deform when pulling or twisting forces are applied without resulting in the pulling off of electrode 10 from skin surface 14 (or further tearing of electrode 10). Of course, the length of the coil can be any length desired, so long as the material is sufficient to withstand anticipated forces.

It is thus a feature of the present invention that the breakaway means or yieldable connection means formed by series 32 allows the bridge portion to be partially pulled apart when applied to the skin surface so that when minimum force or strain is applied tab 42 moves relative to contact portion 20 to absorb the force. In other words, tab 42 is allowed to move with six degrees of freedom (in three linear directions and in three rotational directions) relative to contact portion 20 to prevent contact portion 20 of electrode 10 from being pulled from skin surface 14. And while tab 42 moves relative to contact portion 20, tab 42 maintains electrical contact with insulator layer 26 as the coil or spiral is merely an extension thereof (and of insulator layer 26). The presence of circular aperture 38 also serves stop the tearing effect thereat and spread any associated stress around the circumference thereof. This serves to prevent unwanted tearing of bridge portion 22 both when the minimum force is applied to break connections 36 and even after all connections 36 have been broken.

As shown in FIG. 5, electrodes 10 are preferably provided in a group mounted on a silicone coated carrier 44. The material of the carrier can be either paper, polyester, copoly, polystyrene or like materials, and carrier 44 would preferably be printed with instructions or other information as desired. To use an electrode 10, a selected electrode 10 is thus simply peeled form carrier 44 and applied to the patient using anchor layer 28. Connections 36 are then broken (or before application if desired) and tab 42 is moved to a position so that clip 18 can be attached thereto. Electrode 10 is then ready to function, and bridge portion 22 is ready to relieve exerted forces or strains.

Depicted in FIG. 7 is a first alternative embodiment of an electrode 50 according to the present invention. Electrode 50 is substantially similar to electrode 10, with the primary difference being the particular configuration of series 52 of perforations. In this embodiment, series 52 is formed as two parallel lines, one extending from one lateral side and the other from the other lateral side. The two lines are separated by a predetermined distance sufficient to prevent tearing therebetween, such as ⅛" or more. Clip 18 is then attached to a receptor 54 at the tip of electrode 50, which does not have to be pulled up as with tab 42 but which can simply remain in the plane of electrode 50. Electrode 50 is thus used in the same manner as electrode 10, with the simple configuration of series 52 also allowing receptor 54 to move with six degrees of freedom just as with electrode 10.

Depicted in FIG. 8 is a second alternative embodiment of an electrode 60 according to the present invention. Electrode 60 is substantially similar to electrodes 10 and 50, with the primary difference being the particular configuration of series 62 of perforations. In this embodiment, series 62 is formed as two perpendicular lines, one extending from one lateral side toward the other and the other extending perpendicular thereto and toward receptor 64 but short of the longitudinal side thereat to prevent tearing all the way to the longitudinal side. Clip 18 is then attached to a receptor 64 at the tip of electrode 60, which does not have to be pulled up but which can simply remain in the plane of electrode 60. Electrode 60 is thus used in the same manner as electrode 10, with the simple configuration of series 62 also allowing receptor 64 to move with six degrees of freedom just as with electrodes 10 and 50.

It will also be appreciated that electrodes 10, 50, and 60 can also be used without breaking connections 36 much like the prior electrodes discussed above. In that case, clip 18 is simply attached to bridge portion 22 and perforations 34 will serve to help hold clip 18 to bridge portion 22.

While the present invention has been described with respect to exemplary embodiments thereof, it will be understood by those of ordinary skill in the art that variations and modifications can be effected within the scope and spirit of the invention. Thus, other shapes and configurations of the various elements would be possible beyond those specifically depicted and described which would still provide the same functions or advantages. For example, the receptor and clip could instead be the well known projecting knob and snap fastener. It will also be appreciated that the principles of the present invention are applicable to a variety to electrodes besides those used for biomedical purposes.

What is claimed is:

1. An electrode for establishing electrical connection between a leadwire and a surface comprising:
    a contact portion including a conductive layer, an insulator layer on one side of said conductive layer, and an anchor means on the other side of said conductive layer for anchoring said contact portion to the surface; and
    a conductive bridge portion extending from said contact portion and electrically connected with said conductive layer, said bridge portion including a receptor to which the leadwire is attachable and a breakaway means for allowing said bridge portion to be partially pulled apart when applied to the surface and hence for said receptor to move relative to said contact portion while still maintaining electrical connection with said conductive layer such that when a pulling force is exerted on the contact portion by the surface or the leadwire, the exerted force is relieved by movement of said bridge portion without pulling said contact portion from the surface.

2. An electrode as claimed in claim 1 wherein said bridge portion is an extension of said conductive layer and said insulator layer beyond an end of said anchor means.

3. An electrode as claimed in claim 2 wherein said receptor is a portion of said extension of said conductive layer and said insulator layer.

4. An electrode as claimed in claim 3 wherein said receptor is a tab which is moved from a plane of said extension of said conductive layer and said insulator layer.

5. An electrode as claimed in claim 4 wherein said breakaway means is a series of perforations in said bridge portion.

6. An electrode as claimed in claim 5 wherein said series of perforations form a coil.

7. An electrode as claimed in claim 6 wherein said series of perforations ends in a circular aperture.

8. An electrode as claimed in claim 1 wherein said breakaway means is a series of perforations in said bridge portion.

9. An electrode as claimed in claim 8 wherein said series of perforations ends in a circular aperture.

10. An electrode as claimed in claim 8 wherein said series of perforations form a coil.

11. An electrode as claimed in claim 8 wherein said series of perforations is formed by at least two straight lines.

12. An electrode as claimed in claim 1 wherein said anchor means is a layer of adhesive.

13. An electrode for establishing electrical connection between a leadwire and a surface comprising:
    a flexible contact portion including a conductive layer, an insulator layer on one side of said conductive layer, and an anchor layer on the other side of said conductive layer for anchoring said contact portion to the surface; and
    a conductive bridge portion extending from said contact portion and electrically connected with said conductive layer, said bridge portion including a receptor to which the leadwire is attachable and a yielding connection means for electrically and yieldably connecting said receptor to said contact portion while allowing said receptor to move with six degrees of freedom relative to said contact portion such that when a force is applied to the contact portion by the surface or the leadwire the movement of said receptor helps to relieve the exerted force without pulling said contact portion from the surface.

14. An electrode as claimed in claim 13 wherein said bridge portion includes at least one tear means for allowing said yielding connection means to tear at predetermined locations to form said yielding connection means.

15. An electrode as claimed in claim 14 wherein said tear means is a series of perforations in said yielding connection means.

16. An electrode as claimed in claim 15 wherein said series of perforations form a coil.

17. An electrode as claimed in claim 16 wherein said bridge portion is an extension of said conductive layer and said insulator layer beyond an end of said anchor layer.

18. An electrode as claimed in claim 17 wherein said receptor is a portion of said extension of said conductive layer and said insulator layer.

19. An electrode as claimed in claim 18 wherein said receptor is a tab which is moved from a plane of said extension of said conductive layer and said insulator layer.

20. An electrode as claimed in claim 15 wherein said series of perforations ends in a circular aperture.

* * * * *